United States Patent
Tateno et al.

(10) Patent No.: US 11,905,233 B2
(45) Date of Patent: Feb. 20, 2024

(54) PROCESS FOR PRODUCING UNSATURATED NITRILE

(71) Applicant: ASAHI KASEI KABUSHIKI KAISHA, Tokyo (JP)

(72) Inventors: Eri Tateno, Tokyo (JP); Sho Tamura, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 640 days.

(21) Appl. No.: 17/051,324

(22) PCT Filed: May 15, 2018

(86) PCT No.: PCT/JP2018/018635
§ 371 (c)(1),
(2) Date: Oct. 28, 2020

(87) PCT Pub. No.: WO2019/220521
PCT Pub. Date: Nov. 21, 2019

(65) Prior Publication Data
US 2021/0230102 A1    Jul. 29, 2021

(51) Int. Cl.
| | | |
|---|---|---|
| *C07C 253/24* | (2006.01) | |
| *B01J 8/18* | (2006.01) | |
| *B01J 8/24* | (2006.01) | |
| *B01J 23/30* | (2006.01) | |
| *B01J 35/02* | (2006.01) | |

(52) U.S. Cl.
CPC ........... *C07C 253/24* (2013.01); *B01J 8/1827* (2013.01); *B01J 8/1872* (2013.01); *B01J 8/24* (2013.01); *B01J 23/30* (2013.01); *B01J 35/026* (2013.01); *B01J 2208/00575* (2013.01)

(58) Field of Classification Search
CPC .......................... C07C 253/26; C07C 253/24
See application file for complete search history.

(56) References Cited

U.S. PATENT DOCUMENTS

| 5,914,424 A | 6/1999 | Nakamura et al. |
| 2013/0289298 A1 | 10/2013 | Tateno et al. |

FOREIGN PATENT DOCUMENTS

| CN | 103566838 A | 2/2014 | |
|---|---|---|---|
| JP | 10-139749 A | 5/1998 | |
| JP | 2001-213855 A | 8/2001 | |
| JP | 2005-29528 A | 2/2005 | |
| JP | 2005-193172 A | 7/2005 | |
| JP | 2007-308423 | * 11/2007 | ........... C07D 253/26 |
| JP | 2007-308423 | 11/2007 | |
| JP | 2015-98455 A | 5/2015 | |
| JP | 5779192 B2 | 9/2015 | |
| JP | 2017/512642 A | 5/2017 | |
| WO | WO 2011/090131 A1 | 7/2011 | |
| WO | WO 2015/153192 A1 | 10/2015 | |

OTHER PUBLICATIONS

International Preliminary Report on Patentability and Written Opinion dated Nov. 26, 2020, in PCT/JP2018/018635 (Forms PCT/IB/326, PCT/IB/373, and PCT/ISA/237).
International Search Report (PCT/ISA/210) issued in PCT/JP2018/018635 dated Aug. 14, 2018.
Written Opinion (PCT/ISA/237) issued in PCT/JP2018/018635 dated Aug. 14, 2018.

* cited by examiner

*Primary Examiner* — Paul V Ward
(74) *Attorney, Agent, or Firm* — Birch, Stewart, Kolasch & Birch, LLP

(57) ABSTRACT

A process for producing unsaturated nitrile comprising a reaction step of subjecting hydrocarbon to a vapor phase catalytic ammoxidation reaction in a fluidized bed reactor to produce the corresponding unsaturated nitrile, wherein, in the reaction step, a powder is fed to a dense zone in the fluidized bed reactor using a carrier gas, and a ratio of a linear velocity LV1 of the carrier gas at a feed opening to feed the powder to the fluidized bed reactor to a linear velocity LV2 of a gas in the dense zone (LV1/LV2) is not less than 0.01 and not more than 1200.

6 Claims, 1 Drawing Sheet

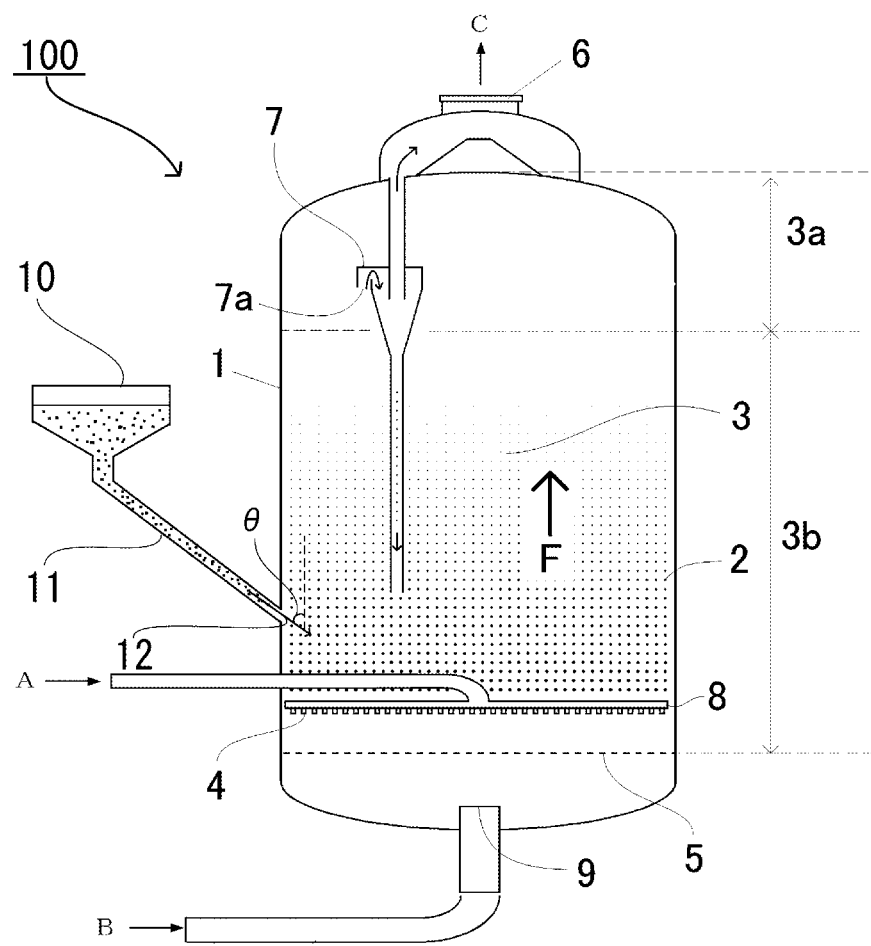

PROCESS FOR PRODUCING UNSATURATED NITRILE

TECHNICAL FIELD

The present invention relates to a process for producing unsaturated nitrile.

BACKGROUND ART

Conventionally, a fluidized bed reactor has been widely used when a hydrocarbon such as an alkane and/or an alkene is subjected to a vapor phase catalytic ammoxidation reaction in the presence of a catalyst. For carrying out such a vapor phase catalytic ammoxidation reaction over a long period of time, various proposals have been made not to decrease the yield of a target product such as acrylonitrile.

For example, Patent Literature 1 discloses, with the intention of providing a production process of acrylonitrile which has a high acrylonitrile yield and a small decrease in acrylonitrile yield over time and is capable of performing stable production for a long period of time, a process for producing acrylonitrile by reacting propylene with molecular oxygen and ammonia in the presence of a catalyst, the process for producing acrylonitrile comprising using a catalyst containing molybdenum, bismuth, iron, nickel, and silica as essential components and maintaining predetermined relations of X-ray diffraction peak intensities derived from various crystal phases after 1000 hours from start of the reaction.

CITATION LIST

Patent Document

Patent Document 1: Japanese Patent Application Laid-Open No. 2005-029528

SUMMARY OF INVENTION

Technical Problem

When a fluidized bed reactor is used for a vapor phase catalytic ammoxidation reaction, a powder catalyst itself and molybdenum contained in the catalyst scatter are discharged from a system, consequently decreasing the yield of unsaturated nitrile. For preventing such a decreased in the yield, the addition of a catalyst and a molybdenum compound into the reaction system can be considered. In that case, the production process described in Patent Document 1 cannot be considered an effective process to suppress the yield decrease of unsaturated nitrile. Alternatively, the addition of a tungsten compound into the reaction system to further enhance a catalytic activity can also be considered. However, when a fluidized bed reactor is used in practice on an industrial scale, only the addition of the catalyst, the molybdenum compound and the tungsten compound into the reaction system is not considered to be necessarily sufficient to suppress a decrease in the yield of unsaturated nitrile or to further enhance the catalytic activity.

The present invention has been made in the light of the above problem, and it is one of the objects of the present invention to provide a process for producing unsaturated nitrile comprising a reaction step of subjecting hydrocarbon to a vapor phase catalytic ammoxidation reaction in a fluidized bed reactor to produce the corresponding unsaturated nitrile, the production process capable of sufficiently suppressing a decrease in the yield of unsaturated nitrile. Another object is to provide a process for producing the unsaturated nitrile, the production process capable of sufficiently enhancing the yield of unsaturated nitrile by the addition of a tungsten compound.

Solution to Problem

The present inventors have conducted extensive studies to achieve the above objects and found the followings. Firstly, when unsaturated nitrile is produced on an industrial scale, powders such as a catalyst segregate at specific areas in a fluidized bed reactor. As a result, utilization efficiency of the powder decreases, thus it is not possible to suppress the yield decrease of unsaturated nitrile or to enhance the yield of unsaturated nitrile by the addition of a tungsten compound. In addition, even when a predetermined amount of a powder such as a catalyst is added into a fluidized bed reactor, an intended amount of the powder does not always function effectively as a part of the catalyst. As a result, it is not possible to suppress a decrease in the yield of unsaturated nitrile or to enhance the yield of unsaturated nitrile by the addition of a tungsten compound. Then, the present inventors have completed the present invention as a result of further studies based on these findings.

That is, the present invention is as follows.

[1] A process for producing an unsaturated nitrile comprising a reaction step of subjecting hydrocarbon to a vapor phase catalytic ammoxidation reaction in a fluidized bed reactor to produce a corresponding unsaturated nitrile, wherein, in the reaction step, a powder is fed to a dense zone in the fluidized bed reactor using a carrier gas, and a ratio of a linear velocity LV1 of the carrier gas at a feed opening to feed the powder to the fluidized bed reactor to a linear velocity LV2 of a gas in the dense zone (LV1/LV2) is not less than 0.01 and not more than 1200.

[2] The process according to [1], wherein 100 times a ratio of a flow rate R1 of the carrier gas to be fed to the fluidized bed reactor to a flow rate R2 of a gas in the fluidized bed reactor (R1/R2) is not less than 0.0005 and not more than 50.

[3] The process according to [1] or [2], wherein the linear velocity LV1 of the carrier gas is not less than 0.01 m/sec and not more than 330 m/sec, and the linear velocity LV2 of the gas in the dense zone is not less than 0.3 m/sec and not more than 1.0 m/sec.

[4] The process according to any one of [1] to [3], wherein the carrier gas is an inert gas.

[5] The process according to any one of [1] to [4], wherein the powder comprises one or more powders selected from the group consisting of a catalytic powder used for the vapor phase catalytic ammoxidation reaction, a powder containing a Mo compound to replenish the catalyst with Mo atoms, and a powder containing a W compound to add W atoms to the catalyst.

[6] The process according to any one of [1] to [5], wherein the feed opening is formed on a side wall in the fluidized bed reactor and a feeding angle of the carrier gas at the feed opening is not less than 15° and not more than 85° to a vertical direction.

[7] The process according to any one of [1] to [6], wherein the linear velocity LV2 of the gas in the dense zone is a linear velocity of a gas stream from the lower part in the vertical direction to the upper part in the vertical direction.

Advantageous Effects of Invention

According to the present invention, a process for producing unsaturated nitrile comprising a reaction step of subjecting hydrocarbon to a vapor phase catalytic ammoxidation reaction in a fluidized bed reactor to produce the corresponding unsaturated nitrile, the production process capable of sufficiently suppressing a decrease in the yield of unsaturated nitrile can be provided. In addition, according to the present invention, the process for producing unsaturated nitrile, capable of sufficiently enhancing the yield of unsaturated nitrile by the addition of a tungsten compound, can be provided.

BRIEF DESCRIPTION OF DRAWINGS

FIG. 1 is a schematic view showing an example of the reactor used in the process for producing unsaturated nitrile of the present embodiment.

DESCRIPTION OF EMBODIMENTS

An embodiment of the present invention (referred simply to as the "present embodiment" hereinafter) is described below in detail in reference to the drawing when needed, but the present invention is not limited to the following embodiments. The present invention can be variously modified without departing from the spirit of the present invention. In the drawings, the same elements are denoted by the same reference characters, and a repeated description thereof may be omitted. Unless otherwise noted, the positional relations such as up and down and left and right are based on the positional relations shown in the drawing. Further, the dimension ratios in the drawing are not limited to the ratios illustrated.

The process for producing unsaturated nitrile of the present embodiment comprises a reaction step of subjecting hydrocarbon to a vapor phase catalytic ammoxidation reaction in a fluidized bed reactor to produce the corresponding unsaturated nitrile, wherein, in the reaction step, a powder is fed to a dense zone in the fluidized bed reactor using a carrier gas and a ratio of a linear velocity LV1 of the carrier gas at a feed opening to feed the powder to the fluidized bed reactor to a linear velocity LV2 of a gas in the dense zone (LV1/LV2) is not less than 0.01 and not more than 1200. Here, the "dense zone" refers to, in the internal space of the fluidized bed reactor during the vapor phase catalytic ammoxidation reaction, a space in which an existing amount of the catalyst (a small amount of a Mo-containing powder and a W-containing powder can be contained as mentioned later) per unit volume is not less than 100 kg/m$^3$ and a space positioned in a lower space of such a space. The dense zone is distinguished from a "sparse zone" positioned in an upper space of such a space and in which an existing amount of the catalyst per unit volume is less than 100 kg/m$^3$. The vapor phase catalytic ammoxidation reaction proceeds mainly in the dense zone.

The reaction step in the present embodiment, hydrocarbon is subjected to a vapor phase catalytic ammoxidation reaction with ammonia in the presence of oxygen in a fluidized bed reactor to produce the corresponding unsaturated nitrile. Examples of the hydrocarbons, the starting material used for the vapor phase catalytic ammoxidation reaction, include alkanes such as methane, ethane, propane, n-butane, and isobutane; and alkenes such as ethylene, propylene, n-butylene and isobutylene. Of these, propane, isobutane, propylene and isobutylene are preferable, and propane and/or propylene is more preferable, from the viewpoint of values of the resulting nitrile compound as an intermediate material for chemicals.

A feed starting material of hydrocarbons and ammonia does not need to be in a high purity and an industrial grade gas can be used. For the feed oxygen source, air, pure oxygen, or air enriched with pure oxygen can be used. Further, as a diluent gas, helium, neon, argon, carbon dioxide gas, water vapor, nitrogen or the like may be fed.

When propane or isobutane is used as the hydrocarbon, the vapor phase catalytic ammoxidation reaction can be carried out under the following conditions.

The molar ratio of the oxygen to be fed to the reaction to propane or isobutane is preferably 0.1 to 6, and more preferably 0.5 to 4. The molar ratio of the ammonia to be fed to the reaction to propane or isobutane is preferably 0.3 to 1.5, and more preferably 0.7 to 1.2. The reaction temperature is preferably 350° C. to 500° C., and more preferably 380° C. to 470° C. The reaction pressure is preferably 5×10$^4$ Pa to 5×10$^5$ Pa, and more preferably 1×10$^5$ Pa to 3×10$^5$ Pa. The contact time of a starting material gas with a catalyst is preferably 0.1 to 10 (sec·g/cc), and more preferably 0.5 to 5 (sec·g/cc).

When propylene or isobutylene is used as the hydrocarbon, the vapor phase catalytic ammoxidation reaction can be carried out under the following conditions.

The molar ratio of propylene to ammonia to oxygen to be fed to the reaction (propylene/ammonia/oxygen) is preferably 1.0/1.0 to 1.5/1.6 to 2.2. The reaction temperature is preferably 380° C. to 480° C. The reaction pressure is preferably 1×10$^5$ Pa to 3×10$^5$ Pa. The contact time of a starting material gas with a catalyst is preferably 2 sec·g/cc to 7 sec·g/cc, and more preferably 3 sec·g/cc to 6 sec·g/cc.

FIG. 1 schematically shows an example of the reactor provided with a fluidized bed reactor which can be used in the process for producing unsaturated nitrile of the present embodiment. A reactor 100 is provided with a fluidized bed reactor 1 to carry out the vapor phase catalytic ammoxidation reaction, a hopper 10 to store one or more powders selected from the group consisting of a powder of catalyst (hereinafter simply referred to as "catalytic powder"), a powder comprising a Mo-containing compound which is a compound comprising Mo (molybdenum) (hereinafter simply referred to as "Mo-containing powder"), and a powder comprising a W-containing compound which is a compound comprising W (tungsten) (hereinafter simply referred to as "W-containing powder") to be fed to the fluidized bed reactor 1, and a feed pipe 11 to connect the fluidized bed reactor 1 and the hopper 10 and feed the above powders from the hopper 10 to the fluidized bed reactor.

Although only one hopper 10 is shown in FIG. 1, a plurality of hoppers may be provided to store the catalytic powder, the Mo-containing powder, and the W-containing powder separately. In the feed pipe 11, a carrier gas flows with the above powders toward the fluidized bed reactor 1 from the hopper 11. The above powders are fed to a dense zone 3b in the fluidized bed reactor 1 by the carrier gas through the feed pipe 11 from a powder feed opening 12 formed in the fluidized bed reactor 1. The powder feed opening 12 may be provided on the side wall of the reactor 1, or may be provided in the internal space of the reactor 1 by laying the feed pipe 11 into the internal space thereof. The carrier gas is not specifically restricted, and examples thereof include inert gases such as nitrogen, helium, and argon, air and carbon dioxide. Of these, inert gases which are inert to the vapor phase catalytic ammoxidation reaction are preferable from the viewpoint of less likely affecting the vapor phase catalytic ammoxidation reaction.

The fluidized bed reactor 1 is installed in such a way that the direction of an arrow F becomes a substantially vertical direction to the ground surface. The fluidized bed reactor 1 has an internal space 3 containing the powder 2 capable of being fluidized therein, a starting material feed opening 4 to feed a starting material gas A comprising hydrocarbon to the internal space 3, and a discharge port 6 to discharge a reaction product gas C from the internal space 3, and a powder feed opening 12 to feed one or more powders selected from the group consisting of a catalytic powder, a Mo-containing powder and a W-containing powder fed from the hopper 10 to the internal space. The internal space 3 has, at the lower side, the dense zone 3b where the vapor phase catalytic ammoxidation reaction mainly proceeds and the powder 2 is densely present and has, at the upper side, the sparse zone 3a where the powder 2 is sparsely present. When the powders are fed from the hopper 10 to the dense zone 3b, the powders can be allowed to effectively come in contact with the catalyst present in the dense zone 3b, thus enhancing the yield of unsaturated nitrile. Most of the powder 2 is catalytic powder but a small amount of the Mo-containing powder and the W-containing powder can be comprised.

The fluidized bed reactor 1 may have a dispersion plate 5 to feed an oxygen-containing gas B comprising oxygen to the internal space 3 and a cyclone 7 to separate and collect the catalyst 2 from the reaction product gas in the internal space 3. The starting material gas A comprising hydrocarbon is fed to the internal space 3 from the starting material feed opening 4 through a dispersion tube 8. The fluidized bed reactor 1 may have a gas feed opening 9 to feed the oxygen-containing gas B. The oxygen-containing gas B introduced into the internal space 3 from the gas feed opening 9 is dispersed by the dispersion plate 5. The starting material gas A to be fed from a plurality of the starting material feed openings 4 and the oxygen-containing gas B to be fed by being dispersed by the dispersion plate 5 are fed in such a way that these gases are opposite to each other, and they are blended while being intermingled with each other.

The powder 2 is fluidized in the internal space 3 with a balance among the weight and the volume density of the powder itself, the feed rates of the starting material gas A and the oxygen-containing gas B (flow rates in the direction of the arrow F), etc. The existing amount (distribution) of the powder 2 per unit space decreases toward the upper part from the lower part of the internal space 3 (in the direction of the arrow F).

The fluidized bed reactor 1 has, in the internal space 3, the cyclone 7 to separate and collect the powder 2 from the reaction product gas. The fluidized bed reactor 1 may additionally have a cooling coil (not shown) to mainly remove heat of reaction of the dense zone 3b of the internal space 3 and thereby control the reaction temperature and a member (not shown) to control the superficial gas velocity in the internal space 3, when needed. The reaction product gas accompanied by the powder 2 enters the cyclone 7 through an inlet 7a. The powder 2 having entered the cyclone 7 falls downward in the internal space 3 so as to be spiral in the conical section of the cyclone 7. On the other hand, the reaction product gas having accompanied the powder is guided to the discharge port 6 by a tube extending upward from the upper part of the cyclone 7. Below the conical portion of the cyclone 7, a tube further extends downward in the internal space 3, and through this tube, the powder 2 is guided downward in the internal space 3.

The superficial gas velocity in the internal space 3 is a linear velocity of a gas stream from the lower part in the vertical direction to the upper part in the vertical direction and varies with a cross-sectional area of the internal space 3 (area in a direction perpendicular to the direction of the arrow F). For example, when an internal space 3 whose cross-sectional areas are not uniform is supposed, the superficial gas velocity decreases at a place having a large cross-sectional area, and the superficial gas velocity increases at a place having a small cross-sectional area. For controlling a superficial gas velocity at a specific zone in the internal space 3, a member may be used. From the viewpoint of control of the superficial gas velocity at each place in the internal space 3, the member is installed in the internal space 3. The gas-flowable cross-sectional area at a place where the member to control the superficial gas velocity is installed is narrowed by a portion occupied by the member to control the superficial gas velocity, so that the superficial gas velocity at this place increases as compared with that at a place where the member to control the superficial gas velocity is not installed. Instead of installing the member to control the superficial gas velocity, the fluidized bed reactor 1 whose diameters are not uniform so that the cross-sectional area of the internal space 3 may vary at the desired place may be used.

In the present embodiment, a ratio of a linear velocity LV1 to a linear velocity LV2 (LV1/LV2) in the vapor phase catalytic ammoxidation reaction in the above reaction step is not less than 0.01 and not more than 1200. Here, the linear velocity LV2 is a linear velocity of the gas in the dense zone 3b of the above superficial gas velocity, the linear velocity LV1 is a linear velocity of the carrier gas at the powder feed opening 12 to feed the powder into the fluidized bed reactor 1. When the LV1/LV2 is not less than 0.01, a desired amount of the powder can be fed without being uneven throughout the entire reactor from the powder feed opening 12 into the fluidized bed reactor 1. As a result, a decrease in the yield of unsaturated nitrile can be sufficiently suppressed, and when the tungsten compound is added, the yield of unsaturated nitrile can be sufficiently enhanced. When the LV1/LV2 is not more than 1200, the powder fed is prevented from being uneven in the fluidized bed reactor 1 enabling the powder to effectively contribute to the reaction. As a result, a decrease in the yield of unsaturated nitrile can be sufficiently suppressed, and when the tungsten compound is added, the yield of unsaturated nitrile can be sufficiently enhanced. From the same viewpoint, the LV1/LV2 is preferably not less than 0.05 and not more than 1100, more preferably not less than 0.10 and not more than 1000, and further preferably not less than 0.70 and not more than 1.7. The LV1/LV2 can be controlled to a predetermined numerical value range by adjusting a linear velocity LV1 and a linear velocity LV2 as mentioned later.

The linear velocity LV1 of the carrier gas is preferably not less than 0.01 m/sec and not more than 330 m/sec. When the linear velocity LV1 is not less than m/sec, the volume of the powder in the feed pipe 11 can be more suppressed and the powder can be fed more precisely to the fluidized bed reactor 1. As a result, a decrease in the yield of unsaturated nitrile can be further sufficiently suppressed, and when the tungsten compound is added, the yield of unsaturated nitrile can be more sufficiently enhanced. When the linear velocity LV1 is not more than 330 m/sec, crushing of the powders at the powder feed opening 12 where powders flowing in the feed pipe 11 merge the powder 2 fluidizing in the feed pipe 11, the fluidized bed reactor 1 and the fluidized bed reactor 1 can be further effectively prevented. For this reason, the powders reduced in size can be much more suppressed from being discharged out of the system. From the same viewpoint, the linear velocity LV1 is more preferably not less than 0.05 m/sec and not more than 300 m/sec, and further preferably not less than m/sec and not more than 250 m/sec. The linear velocity LV1 can be controlled to a predetermined numerical value range by adjusting a feed rate of the starting material gas A to the fluidized bed reactor 1. The linear velocity LV1 of the carrier gas can be calculated from the following formula.

Linear velocity $LV1$ (m/sec)=carrier gas flow rate (Nm$^3$/hr)/cross-sectional area of a circle determined by a pipe diameter of feed pipe 11 (m$^2$)/3600

The linear velocity LV1 can be controlled to a predetermined numerical value range by controlling a flow rate of the carrier gas. When there is a plurality of the feed pipe 11, the LV1 may be determined at each of the feed pipes 11 and controlled so that the LV1 and the LV1/LV2 are within the preferable ranges.

The linear velocity of the gas in the dense zone 3b LV2 is preferably not less than 0.3 m/sec and not more than 1.0 m/sec. When the linear velocity LV2 is not less than 0.3 m/sec, the powder from the feed pipe 11 can be further effectively in contact with the powder 2 fluidizing in the fluidized bed reactor 1. As a result, a decrease in the yield of unsaturated nitrile can be further sufficiently suppressed, and when the tungsten compound is added, the yield of unsaturated nitrile can be more sufficiently enhanced. When the linear velocity LV2 is not more than 1.0 m/sec, crushing of the powders at the powder feed opening 12 where powders flowing in the feed pipe 11 merge the powder 2 fluidizing in the fluidized bed reactor 1 and the fluidized bed reactor 1 can be further effectively prevented. For this reason, the powders reduced in size can be much more suppressed from being discharged out of the system. From the same viewpoint, the linear velocity LV2 is more preferably not less than 0.35 m/sec and not more than 0.90 m/sec, and further preferably not less than 0.4 m/sec and not more than 0.85 m/sec. The linear velocity LV2 of the gas in the dense zone 3b can be calculated from the following formula. Here, the "effective cross-sectional area in the dense zone 3b" refers to a cross-sectional area in a direction perpendicular to the direction of the gas flowing in the dense zone 3b, and when the member to control the superficial gas velocity and the linear velocity LV2 is present, the area from which the portion thereof is excluded is referred. The "gas flow rate R2" is determined by the total amount of gases fed to the internal space, such as the starting material gas, the oxygen-containing gas, and the carrier gas.

Linear velocity $LV2$(m/sec)=gas flow rate $R2$(Nm$^3$/hr)/smallest area of effective cross-sectional areas(m$^2$) in dense zone 3b/3600

The linear velocity LV2 can be controlled to a predetermined numerical value range by adjusting the gas flow rate and/or effective cross-sectional area.

In the process for producing unsaturated nitrile of the present embodiment, the linear velocity LV2 of the gas in the dense zone 3b is a linear velocity of a gas stream from the lower part in the vertical direction to the upper part in the vertical direction in the dense zone 3b. When such a linear velocity LV2 is controlled in such a way as to be within the above-mentioned numerical value range, a decrease in the yield of unsaturated nitrile can be further effectively and surely suppressed, and when the tungsten compound is added, the yield of unsaturated nitrile can be sufficiently enhanced.

In the process for producing unsaturated nitrile of the present embodiment, 100 times a ratio of a flow rate R1 (Nm$^3$/hr) of the carrier gas to be fed to the fluidized bed reactor 1 to a flow rate R2 (Nm$^3$/hr) of the gas in the internal space 3 (R1/R2) is preferably not less than 0.0005 and not more than 50. Here, the "flow rate R1 of the carrier gas" is a carrier gas flow rate (Nm$^3$/hr) flowing in the feed pipe 11, and refers to the total amount of the carrier gas flow rate in each of the feed pipes in the case that there is a plurality of the feed pipe 11. The "gas flow rate R2" is determined by the total amount of gases fed to the internal space, such as the starting material gas, the oxygen-containing gas, and the carrier gas.

When the value of 100 times a ratio R1/R2 is not less than 0.0005, a desired amount of the powder can be fed evenly throughout the entire reactor from the powder feed opening 12 into the fluidized bed reactor 1. As a result, a decrease in the yield of unsaturated nitrile can be sufficiently suppressed, and when the tungsten compound is added, the yield of unsaturated nitrile can be sufficiently enhanced. When the value of 100 times a ratio R1/R2 is not more than 50, the powder fed is more surely prevented from being uneven in the fluidized bed reactor 1 enabling the powder to further effectively contribute to the reaction. As a result, a decrease in the yield of unsaturated nitrile can be sufficiently suppressed, and when the tungsten compound is added, the yield of unsaturated nitrile can be sufficiently enhanced. Additionally, the fluctuation of temperature in the fluidized bed reactor 1 caused by the carrier gas and the powder fed to the fluidized bed reactor 1 can be prevented. As a result, a decrease in the yield of unsaturated nitrile caused by the fluctuation of reaction temperature can be further surely prevented.

The value of R1 can be suitably controlled by the scale of the reactor and powder feeder but is preferably not less than 0.05 Nm$^3$/hr and not more than 50000 Nm$^3$/hr, and more preferably not less than 0.1 Nm$^3$/hr and not more than 30000 Nm$^3$/hr. When the value of R1 is not less than 0.05 Nm$^3$/hr, a desired amount of the powder can be fed without being more uneven in desired time throughout the entire reactor. As a result, a decrease in the yield of unsaturated nitrile can be sufficiently suppressed, and when the tungsten compound is added, the yield of unsaturated nitrile can be sufficiently enhanced. When the value of R1 is not more than 50000 Nm$^3$/hr, the powder fed can be more surely prevented from being uneven in the fluidized bed reactor 1 enabling the powder to further effectively contribute to the reaction. As a result, a decrease in the yield of unsaturated nitrile can be sufficiently suppressed, and when the tungsten compound is added, the yield of unsaturated nitrile can be sufficiently enhanced. Additionally, the fluctuation of temperature in the fluidized bed reactor 1 caused by the carrier gas and the powder fed to the fluidized bed reactor 1, can be prevented. As a result, a decrease in the yield of unsaturated nitrile caused by the fluctuation of reaction temperature can be further surely prevented.

The fluctuation range of the reaction temperature is, from the viewpoint of reducing the influence on the yield decrease of unsaturated nitrile, preferably less than 20° C., and more preferably less than 10° C. The fluctuation range of the reaction temperature is, between the start of charging the powder into the fluidized bed reactor 1 and the completion of charge, the largest value in temperature change since before charge. The fluctuation range of reaction temperature can be measured using a thermometer installed in the dense zone in the internal space 3. The installation location of the thermometer is not restricted as long as it is in the zone of the dense zone but for obtaining average information, it is preferable to install multiple thermometers in the zone of the dense zone and define the fluctuation range calculated from the average value of the temperature at these measurement locations.

In the process for producing unsaturated nitrile of the present embodiment, the feeding angle (reference sign in FIG. 1) of the carrier gas at the powder feed opening 12 is preferably not less than 15° and not more than 85° to a vertical direction. When the feeding angle is not less than 15° to a vertical direction, the powder fed from the powder feed opening 12 can be more effectively and more surely suppressed from being unevenly present near the powder feed opening 12. As a result, the vapor phase catalytic ammoxidation reaction can be further sufficiently prevented from locally proceeding or not proceeding, further enhancing the yield of unsaturated nitrile, while making it easier to control the reaction. When the feeding angle θ is not more than 85° to a vertical direction, the powder can be fed more effectively and more surely to the dense zone 3b having a high existing density of the powder and hence powders newly added to the entire powder 2 present in the fluidized bed reactor 1 can be homogeneously mixed. As a result thereof, the vapor phase catalytic ammoxidation reaction can be further sufficiently prevented from locally proceeding or not proceeding, further enhancing the yield of unsaturated nitrile, while making it easier to control the reaction.

The catalyst according to the present embodiment escapes from the fluidized bed reactor 1 during the catalytic ammoxidation reaction and the performance decreases as the reaction proceeds. Thus, from the viewpoint of retaining a catalytic amount in the fluidized bed reactor 1 at a constant amount or more while much more suppressing the yield decrease of unsaturated nitrile, it is preferable to feed a catalytic powder to the fluidized bed reactor 1 from the powder feed opening 12. The feed rate of a catalytic powder is, from the same viewpoint as above, preferably not less than 0.02 kg and not more than 2 kg, and more preferably not less than 0.05 kg and not more than 1.5 kg, per ton of the catalyst in the fluidized bed reactor 1 per day. When the feed rate of the catalytic powder is not less than the above lower limit value, effects are exerted such as a catalytic amount in the reactor can be retained at a constant amount or more and the yield decrease of unsaturated nitrile can be further suppressed. When the feed rate of the catalytic powder is not more than the above upper limit value, effects are exerted such as a catalytic amount in the reactor can be controlled within the appropriate range and the yield of unsaturated nitrile can be more effectively maintained.

The composition of the catalyst is not specifically restricted as long as it has an activity against the vapor phase catalytic ammoxidation reaction, but from the viewpoint that the action and effect of the present invention are exerted more effectively and more surely, an oxide catalyst comprising at least molybdenum as an element is preferable. More specifically, for the ammoxidation reaction of propane or isobutane, a catalyst having a composition represented by the following formula (1) can be mentioned.

(1)

Here, in the formula (1), a, b, c, d, e and n each represent an atomic ratio of each atom per Mo atom, and are in the ranges of $0.01 \leq a \leq 1$, $0.01 \leq b \leq 1$, $0.01 \leq c \leq 1$, $0 \leq d < 1$, and $0 \leq e < 1$, and n is a value satisfying a balance of the valences.

Per Mo atom, the atomic ratio a of V is preferably not less than 0.1 but less than 0.4, and the atomic ratio b of Nb is preferably not less than 0.01 but less than 0.2. The atomic ratio c of the X component per Mo atom is preferably not less than 0.01 but less than 0.6, and is more preferably not less than 0.1 but less than 0.4.

Examples of the element represented by X include one or more elements selected from, for example, Sb (antimony) and Te (tellurium). Examples of compounds containing these elements include nitrates, carboxylates, carboxylic acid ammonium salts, peroxocarboxylates, peroxocarboxylic acid ammonium salts, halogenated ammonium salts, halides, acetylacetonates and alkoxides. Of these, aqueous starting materials represented by nitrates and carboxylates are preferably used.

In the industrial production process for unsaturated nitrile, properties of withstanding long-term use at not lower than 400° C. are generally required, and it is particularly preferable to use Sb as the element represented by X. On the other hand, in the industrial production process for an unsaturated acid, a reaction at not higher than 400° C. is also possible, and therefore, influence by escaping of Te in the long-term operation is small, so that also Te can be preferably used.

d that is an atomic ratio of an element represented by T per Mo atom is preferably not less than 0 but less than 1, more preferably not less than 0.001 but less than 0.1, and still more preferably not less than 0.002 but less than 0.08. The element represented by T is preferably one or more elements selected from the group consisting of Ti (titanium), Zr (zirconium), Hf (hafnium), Ta (tantalum), Cr (chromium), W (tungsten), Mn (manganese), Re (rhenium), Fe (iron), Co (cobalt), Ni (nickel), Pd (palladium), Pt (platinum), Ag (silver), Au (gold), Zn (zinc), B (boron), Al (aluminum), Ga (gallium), In (indium), Ge (germanium), Sn (tin), Pb (lead), P (phosphorus) and Bi (bismuth), and is more preferably Ti, W or Mn.

e that is an atomic ratio of an element represented by Z per Mo atom is preferably not less than 0 but less than 1, and more preferably not less than 0.0001 but less than 0.5. As the elements represented by Z, preferable are Sr (strontium), Ba (barium), Sc (scandium), Y (yttrium), La (lanthanum), Ce (cerium), Pr (praseodymium) and Yb (ytterbium), and particularly preferable is Ce. From the viewpoint of enhancement in yield of unsaturated nitrile in the ammoxidation reaction, it is preferable that the oxide catalyst contain an element represented by Z, and it is more preferable that the elements be homogeneously dispersed in a catalyst particle. However, as the element represented by Z is likely to cause an unpreferable reaction in the slurry as taught in Japanese Patent Laid-Open No. 11-244702, its content is preferably very small.

Examples of compounds containing Mo, which become starting materials for Mo in the catalyst, (referred to as "Mo-containing compounds" hereinafter, the same shall apply to other elements) include molybdenum trioxide, ammonium heptamolybdate, phosphomolybdic acid and silicomolybdic acid, and of these, ammonium heptamolybdate [$(NH_4)_6Mo_7O_{24} \cdot 4H_2O$] can be preferably used.

Examples of V-containing compounds that become starting materials for V in the catalyst include vanadium pentoxide, ammonium metavanadate and vanadyl sulfate, and of these, ammonium metavanadate [$NH_4VO_3$] can be preferably used.

Examples of Nb-containing compounds that become starting materials for Nb in the catalyst include niobic acid, inorganic acid salts of niobium and organic acid salts of niobium, and of these, niobic acid can be preferably used.

When Te is used as an element represented by X, telluric acid [$H_6TeO_6$] can be preferably used as a starting material for Te in the catalyst, and when Sb is used, antimony oxide, particularly antimony trioxide [$Sb_2O_3$], can be preferably used as a starting material for Sb in the catalyst.

For the vapor phase ammoxidation reaction of propylene or isobutylene, for example, catalysts having the compositions represented by the following formulae (2) and (3) can be mentioned.

$$Mo_{12}Bi_aFe_bJ_cD_dE_eL_fG_gO_n \qquad (2)$$

Here, in the formula (2), J represents one or more elements selected from the group consisting of Ni, Co, Mn, Zn, Mg, Ca, Sr and Ba; D represents one or more elements selected from the group consisting of Cr, W, V, Nb, B, Al, Ga, In, P, Sb and Te; E represents one or more elements selected from the group consisting of rare earth elements; L represents one or more elements selected from the group consisting of Ru, Rh, Pd, Os, Ir and Pt; G represents one or more elements selected from the group consisting of Na, K, Rb and Cs; a, b, c, d, e, f, g and n represent, respectively, atomic ratios of bismuth (Bi), iron (Fe), elements represented by J, elements represented by D, elements represented by E, elements represented by L, elements represented by G and oxygen (O) to 12 atoms of molybdenum (Mo); a is not less than 0.05 and not more than 7; b is not less than 0.1 and not more than 7; c is not less than 0 and not more than 12; d is not less than 0 and not more than 5; e is not less than 0 and not more than 5; f is not less than 0 and not more than 0.2; g is not less than 0.01 and not more than and n is the number of oxygen atoms satisfying the valences of constituent elements other than oxygen.

$$Mo_{12}(Bi_{1-a}Ce_a)_bFe_cX_dT_eZ_fO_g \qquad (3)$$

Here, in the formula (3), X represents one or more elements selected from the group consisting of Ni and Co, T represents one or more elements selected from the group consisting of Mg, Ca, Zn, Sr and Ba, Z represents one or more elements selected from the group consisting of K, Rb and Cs, a represents a relative atomic ratio of Ce to the total of Bi and Ce and is not less than 0.2 and not more than 0.8, b represents the total atomic ratio of Bi and Ce to 12 atoms of molybdenum (Mo) and is not less than and not more than 1.5, c represents an atomic ratio of Fe to 12 atoms of Mo and is not less than 0.1 and not more than 3, d represents an atomic ratio of X to 12 atoms of Mo and is not less than 0.1 and not more than 9.5, e represents an atomic ratio of T to 12 atoms of Mo and is not less than 0 and not more than 9.5, f represents an atomic ratio of Z to 12 atoms of Mo and is not less than 0.01 and not more than 2, and g represents an atomic ratio of oxygen to 12 atoms of Mo and the number of oxygen atoms required to satisfy the valences of other elements present.

For salts or compounds containing these elements, ammonium salts, nitrates, carboxylates, carboxylic acid ammonium salts, peroxocarboxylates, peroxocarboxylic acid ammonium salts, halogenated ammonium salts, halides, acetylacetonates and alkoxides can be typically used, and aqueous starting materials such as nitrates and carboxylates are preferable.

Examples of the Mo-containing compounds, which become starting materials for Mo in the catalyst, include molybdenum trioxide, ammonium heptamolybdate, phosphomolybdic acid and silicomolybdic acid, and of these, ammonium heptamolybdate [$(NH_4)_6Mo_7O_{24} \cdot 4H_2O$] can be preferably used.

The catalyst in the present embodiment may be a catalyst containing silica, more specifically, a silica-supported catalyst which is supported on silica. When the catalyst is an oxide catalyst, the content of silica contained in the silica-supported catalyst, preferably the content of the support silica, is preferably, from the viewpoint of enhancing the strength of the catalyst, not less than 20 mass % in terms of $SiO_2$ to the total mass of the silica-supported catalyst containing an oxide and silica. Additionally, the content thereof is preferably, from the viewpoint of imparting a sufficient activity, not more than 70 mass % in terms of $SiO_2$ to the total mass of the silica-supported catalyst containing an oxide and silica. The content thereof is more preferably not less than 40 mass % and not more than 65 mass % in terms of $SiO_2$ to the total mass of the silica-supported catalyst containing an oxide and silica.

When the oxide catalyst is supported on silica, silica sol, powder silica or the like can be added as a starting material for silica. The powder silica is preferably one produced by a pyrogenic method, and by dispersing the powder silica in water in advance and using the resulting dispersion, addition to a slurry and mixing become easy. The dispersing method is not specifically restricted, and dispersing of the powder silica can be carried out using a general homogenizer, a homomixer, an ultrasonic vibrator, etc. singly or in combination.

Molybdenum in the catalyst according to the present embodiment escapes from the reactor during the vapor phase catalytic ammoxidation reaction, so the molybdenum content in the oxide catalyst, unless done anything in particular, tends to decrease. Thus, it is preferable to feed a Mo-containing powder to the fluidized bed reactor 1 from the powder feed opening 12 so that a decrease in the molybdenum content in the catalyst present in the fluidized bed reactor 1 can be suppressed.

The feed rate of the Mo-containing powder to the fluidized bed reactor 1 is not specifically restricted but is preferably not less than 0.02 kg and not more than 2 kg, and more preferably not less than 0.05 kg and not more than 1 kg, per ton of the catalyst in the fluidized bed reactor 1 per day. When the Mo-containing compound in an amount within the above range is fed, an amount of molybdenum meeting an amount of escaping from the catalyst is fed to the reactor and thereby the molybdenum amount in the catalyst is maintained, making it easier to prevent the yield from decreasing. When the feed rate is not more than the upper limit value, ammonia in the reaction gas burns due to extra molybdenum compounds and decomposed products thereof, more effectively and more surely suppressing the wasteful consumption of ammonia. Unstable reaction temperatures caused by temperature increases in the fluidized bed reactor 1 can also be easily prevented.

The Mo-containing compound in the Mo-containing powder to be fed to the fluidized bed reactor 1 can be a general compound and examples include ammonium heptamolybdate ($(NH_4)_6Mo_7O_{24} \cdot 4H_2O$), molybdenum trioxide ($MoO_3$), phosphomolybdic acid ($H_3PMo_{12}O_{40}$), silicomolybdic acid ($H_4SiMo_{12}O_{40}$), and molybdenum(V) chloride ($MoCl_5$). Of these, ammonium heptamolybdate ($(NH_4)_6Mo_7O_{24} \cdot 4H_2O$) is preferable. Ammonium heptamolybdate easily decomposes after added and is thus more easily taken into the catalyst and has small negative influence on the catalyst by counter ions of molybdenum in the Mo-containing compound or the like. Based on these, when ammonium heptamolybdate is used, the effect on the yield maintenance of unsaturated nitrile tends to be much more easily obtained.

The catalyst according to the present embodiment has a catalytic activity as it is. However, when the W-containing compound is caused to come in contact with the catalyst during the vapor phase catalytic ammoxidation reaction using the fluidized bed reactor 1, the selectivity of unsaturated nitrile can be enhanced. For example, the selectivity of unsaturated nitrile may be insufficient under the condition where a starting material gas is fed to the fluidized bed reactor 1 holding the catalyst and the vapor phase catalytic ammoxidation reaction is allowed to proceed. Even in such a case, the selectivity can be more enhanced than the initial condition by feeding the W-containing powder while proceeding the reaction.

In the production process of the present embodiment, the amount of the W-containing compound to be fed when the W-containing powder is fed to the fluidized bed reactor 1 is preferably in such a way that a molar ratio of tungsten contained in the W-containing compound to molybdenum contained in the catalyst (W/Mo ratio) is not less than 0.0001 and not more than 0.1 in the fluidized bed reactor 1. When a W/Mo ratio is not less than 0.0001 in the fluidized bed reactor 1, contact frequency between the catalyst and the W-containing compound increases and metals such as molybdenum in the catalyst and tungsten can be more efficiently exchanged. On the other hand, when the W/Mo ratio is not more than 0.1, burning of excessive ammonia is more effectively suppressed and the yield decrease of unsaturated nitrile can be further suppressed. After feeding the W-containing compound, it is preferable that a molar ratio of Wc, which is the difference between the amount of tungsten contained in the catalyst after feeding the W-containing compound and the amount of tungsten contained in the catalyst before feeding in the fluidized bed reactor 1, to the amount of molybdenum contained in the catalyst (Wc/Mo ratio) be not less than 0.0001 and not more than 0.1.

As mentioned above, tungsten can be contained as the element constituting the catalyst. Even in such a case, the selectivity of unsaturated nitrile can be enhanced by feeding the W-containing powder to the fluidized bed reactor 1. The present inventors presume the reason for this is caused that the W-containing compound to be fed to the fluidized bed reactor 1 is involved with reforming near the surface of catalyst and provides an action different from the tungsten component entered into crystals of the catalyst. However, factors are not limited thereto.

More specifically, it is assumed that when the W-containing compound is fed to the fluidized bed reactor 1, the catalyst and the tungsten compound come in contact and the W-containing compound spreads particularly on the surface of the catalyst by the solid phase reaction, thereby causing the exchange reaction with metal elements such as Mo. The present inventors consider that this exchange reaction contributes to the selectivity improvement of unsaturated nitrile.

The method for achieving the above W/Mo ratio within the predetermined numerical value range is not specifically restricted but it is preferable to feed the W-containing powder and/or the Mo-containing powder to the fluidized bed reactor 1 suitably from the hopper 10 through the powder feed pipe 11 as mentioned above. The feed frequency and the amount to be fed at one feed can be suitably determined as long as the W/Mo ratio maintains not less than 0.0001 and not more than 0.1.

The particle diameter of the powder to be fed to the fluidized bed reactor 1 is not specifically restricted but, for example, it is not less than 1 μm and not more than 500 μm in terms of average particle diameter. The volume density of the powder is not specifically restricted but, for example, it is not less than 0.1 g/cm$^3$ and not more than 10.0 g/cm$^3$ at 25° C.

The dimension of the fluidized bed reactor used for the process for producing unsaturated nitrile of the present embodiment is not specifically restricted and, for example, a reactor having a reactor inner diameter of not less than 0.5 mg) and not more than 20 mg) at the section corresponding to the dense zone can be used. In the process for producing unsaturated nitrile of the present embodiment, when an industrial scale large fluidized bed reactor is specifically used, the action and effect of the present invention can be provided more effectively and more surely. That is to say, the unevenness of the powder and accumulation of the powder in the feed pipe are likely to occur in an industrial scale large fluidized bed reactor compared with a small fluidized bed reactor (for example, a pilot plant and lab-scale). However, in the process for producing unsaturated nitrile of the present embodiment, the unevenness of the powder can be more effectively suppressed even in such a large fluidized bed reactor and the accumulation of the powder in the feed pipe can be more effectively prevented. As a result, a decrease in the yield of unsaturated nitrile can be sufficiently suppressed, and when the tungsten compound is fed, the selectivity of unsaturated nitrile and even the yield of unsaturated nitrile can be sufficiently enhanced. The dimension of such a large fluidized bed reactor is within, for example, a reactor inner diameter of not less than 3 mφ) and not more than 20 mφ).

Example 1

The present invention will be described in further detail below with reference to Examples but the present invention is not limited to these Examples.

Example 1

A first reactor having the same structure as shown in FIG. 1, except that the powder feed opening 12 is positioned between the dispersion plate 5 and the dispersion tube 8, was prepared. The fluidized bed reactor 1 was in the form of a vertical cylinder having an inner diameter of 0.6 m and a length of 15 m. The hopper 10 and the fluidized bed reactor 1 were connected through the powder feed pipe 11 in such a way that the center of the powder feed opening 12 (a cross-sectional area of the circle determined from a pipe diameter of the feed pipe 11: 0.0006 m$^2$) was positioned at the height of 0.14 m from a lower end of the internal space 3 (the dispersion plate 5). The interspace between the dispersion tube 8 and the dispersion plate 5 was 0.26 m and a feeding angle θ of the carrier gas at the powder feed opening 12 was 45°.

The fluidized bed reactor 1 was filled with 580 kg of a catalyst $(Ma_{1.0}V_{0.214}Sb_{0.220}Nb_{0.105}W_{0.030}Ce_{0.005}O_n/50.0$ wt %-SiO$_2$) described in Example 1 of Japanese Patent No. 5779192. Propane and ammonia as reaction starting materials were fed from the starting material feed opening 4 and air was fed from the dispersion plate 5 through the gas feed opening 9 in such a way that the propane:ammonia:air molar ratio became 1:1:15 at a reaction temperature of 445° C. and an normal reaction pressure to start the vapor phase catalytic ammoxidation reaction. A powder of WO$_3$ (average particle diameter: 45 μm, volume density: 2.0 g/cm$^3$) was held in the hopper 10 as the W-containing powder. When the catalytic performance was stabilized after the vapor phase catalytic ammoxidation reaction started, 0.4 kg of the WO$_3$ powder was fed to the fluidized bed reactor 1 with nitrogen, a carrier gas, from the powder feed opening 12 through the feed pipe 11. At this time, the flow rate of nitrogen was controlled so that the linear velocity LV1 became as shown in Table 1. The linear velocity LV2 became the amount shown in Table 1, when the amounts of air, propane and ammonia were controlled. At this time, the smallest area of the effective cross-sectional areas in the dense zone of the fluidized bed reactor 1 was 0.25 m². The flow rate R1 of nitrogen, the carrier gas, in the feed pipe 11 was 11 m³/hr, and the flow rate R2 of the gas in the internal space 3 was 450 m³/hr. Thereafter, 0.4 kg each of the $WO_3$ powder every 5 days, total of 6 times in 25 days, was fed to the fluidized bed reactor 1 while the vapor phase catalytic ammoxidation reaction was continued. A zone where the dense zone was present was determined from the differential pressure and the height of differential pressures measurement locations in the fluidized bed reactor 1 using the following formula and an upper end of the dense zone was found at the position of 7 m from the lower end of the internal space 3 (the dispersion plate 5).

(Existing amount of catalyst per unit volume between height $h1$ and height $h2$ (higher than height $h1$)=(differential pressure between $h2$ and $h1$)/(distance between $h2$ and $h1$)

Here, the height h1 is the height of the dispersion plate 5. In Table 1, the height from the lower end of the internal space 3 (the dispersion plate 5) is shown as "Upper end of dense zone".

Firstly, the catalyst immediately before the powder was fed and the catalyst 30 days after the reaction started were collected to determine the respective compositions by fluorescent X-ray analysis. The total amount of the powders fed to the fluidized bed reactor 1 for 30 days was defined as "theoretical increased amount", and the percentage of a ratio of an "actual increased amount" represented by the following formula to the theoretical increased amount (kg) (actual increased amount/theoretical increased amount) was derived as utilization efficiency. The higher this utilization efficiency is, it means that the powder was fed to the fluidized bed reactor 1 as desired. The "$WO_3$ amount" in the formula below means an amount obtained by converting the amount of W determined from the fluorescence X-ray analysis to $WO_3$. The results are shown in Table 1.

Actual increased amount (kg)=($WO_3$ amount contained in catalyst after 30 days had passed since reaction started (mass %)–$WO_3$ amount contained in catalyst immediately before powder was first fed (mass %))×catalyst amount in fluidized bed reactor 1 (kg)

A yield of acrylonitrile immediately after the vapor phase catalytic ammoxidation reaction started and a yield of acrylonitrile 30 days after the start of the reaction were derived. The degree of the increase in the yield of acrylonitrile 30 days after the start of the reaction was investigated based on the yield of acrylonitrile immediately after the start and evaluated as a "yield improvement range". The larger this yield improvement range is, it means a catalytic activity was enhanced. Additionally, the temperature fluctuation range in the fluidized bed reactor 1 when the powder was fed was recorded as the average value of indicated values of the thermometers at 4 locations installed 50 mm above the dispersion plate in the dense zone of the reactor internal space 3. The results are shown in Table 1.

Examples 2 to 6, 8 to 10, and Comparative Examples 1 and 2

Utilization efficiency, yield improvement range and temperature fluctuation range were evaluated in the same manner as in Example 1, except that the linear velocities LV1 and LV2 were changed in such a way as to be the numerical values shown in Table 1. The results are shown in Table 1.

Example 7

Utilization efficiency, yield improvement range and temperature fluctuation range were evaluated in the same manner as in Example 1, except that the linear velocity LV2 was changed in such a way as to be the numerical value shown in Table 1 by installing a member in the dense zone of the fluidized bed reactor 1 so that the smallest area of the effective cross-sectional areas was 0.22 m².

Examples 11 to 18 and Comparative Examples 3 and 4

Utilization efficiency and yield improvement range were evaluated in the same manner as in Example 1, except that the powder held in the hopper 10 and fed to the fluidized bed reactor 1 was changed from the $WO_3$ powder to ammonium heptamolybdate (AHM) powder and the linear velocities LV1 and LV2 and the feed rate of the powder were changed as shown in Table 1. The "actual increased amount" determined as below was used, and the "AHM amount" in the formula below means an amount obtained by converting the amount of Mo determined by the fluorescent X-ray analysis to AHM.

Actual increased amount (kg)=($AHM$ amount contained in catalyst after 30 days had passed since reaction started (mass %)–AHM amount contained in catalyst immediately before powder was first fed (mass %))×catalyst amount in fluidized bed reactor 1 (kg)

Examples 19 to 26 and Comparative Examples 5 and 6

Yield improvement range and temperature fluctuation range were evaluated in the same manner as in Example 1, except that the powder held in the hopper 10 and fed to the fluidized bed reactor 1 was changed from the $WO_3$ powder to the catalytic powder and the linear velocities LV1 and LV2 and the feed rate of the powder were changed as shown in Table 1. The results are shown in Table 1.

Example 27

A second reactor having the same structure as shown in FIG. 1 was prepared. The fluidized bed reactor 1 was in the form of a vertical cylinder having an inner diameter of 8 m and a length of 20 m. The hopper 10 and the fluidized bed reactor 1 were connected through the powder feed pipe 11 in such a way that the center of the powder feed opening 12 (a cross-sectional area of the circle determined from a pipe diameter of the feed pipe 11: 0.019 m²) was positioned at the height of 0.40 m from a lower end of the internal space 3 (the dispersion plate 5.) The interspace between the dispersion tube 8 and the dispersion plate 5 was 0.39 m and a feeding angle θ of the carrier gas at the powder feed opening 12 was 45°. The fluidized bed reactor 1 was filled with 100 ton of a catalyst described in Example 1 of Japanese Patent No. 5779192. Propane and ammonia that were reaction starting materials were fed from the starting material feed opening 4 and air was fed from the dispersion plate 5 through the gas feed opening 9 in such a way that the propane:ammonia:air molar ratio became 1:1:15 at a reaction temperature of 445°

C. and an ordinary reaction pressure to start the vapor phase catalytic ammoxidation reaction. A powder of WO$_3$ (average particle diameter: 45 μm, volume density: 2.0 g/cm$^3$) was held in the hopper 10 as the W-containing powder. When the catalytic performance was stabilized since the vapor phase catalytic ammoxidation reaction started, 250 kg of the WO$_3$ powder was fed to the fluidized bed reactor 1 with nitrogen, a carrier gas, from the powder feed opening 12 through the feed pipe 11. At this time, a flow rate of nitrogen was controlled so that a linear velocity LV1 became as shown in Table 1. A linear velocity LV2 was the amount shown in Table 1 when the amounts of air, propane and ammonia were controlled. At this time, the smallest area of the effective cross-sectional areas in the dense zone of the fluidized bed reactor 1 was 67.3 m$^2$. A flow rate R1 of nitrogen, the carrier gas, in the feed pipe 11 was 800 m$^3$/hr, and a flow rate R2 of the gas in the internal space 3 was 120000 m$^3$/hr. Thereafter, 250 kg each of the WO$_3$ powder every 5 days, total of 6 times in 25 days, was fed to the fluidized bed reactor 1 while the vapor phase catalytic ammoxidation reaction was continued. A zone where the dense zone was present was determined from the differential pressure and the height of differential pressures measurement locations in the fluidized bed reactor 1 by the same manner in Example 1 and an upper end of the dense zone was found at the position of 13 m from the lower end of the internal space 3 (the dispersion plate 5). In Table 1, the height from the lower end of the internal space 3 (the dispersion plate) is shown as "Upper end of dense zone". The temperature fluctuation range was recorded as the average value of indicated values of the thermometers at 4 locations installed 800 mm above the dispersion plate.

Examples 28 to 32 and Comparative Examples 7 and 8

Utilization efficiency, yield improvement range and temperature fluctuation range were evaluated in the same manner as in Example 1, except that the powder held in the hopper 10 and fed to the fluidized bed reactor 1 was changed from the WO$_3$ powder to ammonium heptamolybdate (AHM) powder and the linear velocities LV1 and LV2 and the feed rate of the powder were changed as shown in Table 1. The results are shown in Table 1.

Examples 33 and 34

Utilization efficiency, yield improvement range and temperature fluctuation range were evaluated in the same manner as in Example 15, except that the feeding angle θ was changed to the values shown in Table 1. The results are shown in Table 1.

TABLE 1

| | LV1 (m/sec) | LV2 (m/sec) | LV1/LV2 | R1 (m$^3$/hr) | R2 (m$^3$/hr) |
|---|---|---|---|---|---|
| Example 1 | 0.6 | 0.7 | 0.86 | 11 | 450 |
| Example 2 | 0.4 | 0.8 | 0.50 | 11 | 514 |
| Example 3 | 0.85 | 0.45 | 1.89 | 11 | 289 |
| Example 4 | 0.6 | 1.2 | 0.50 | 11 | 771 |
| Example 5 | 5 | 0.7 | 7.14 | 20 | 450 |
| Example 6 | 5 | 0.8 | 6.25 | 20 | 500 |
| Example 7 | 5 | 0.8 | 6.25 | 20 | 450 |
| Example 8 | 85 | 0.45 | 188.89 | 230 | 450 |
| Example 9 | 1 | 0.45 | 2.22 | 12.9 | 289 |
| Example 10 | 0.2 | 0.8 | 0.25 | 5.5 | 514 |
| Comparative Example 1 | 338 | 0.264 | 1280.30 | 400 | 150 |
| Comparative Example 2 | 0.008 | 1 | 0.008 | 0.15 | 570 |
| Example 11 | 0.6 | 0.7 | 0.86 | 11 | 450 |
| Example 12 | 0.4 | 0.8 | 0.50 | 11 | 514 |
| Example 13 | 0.85 | 0.45 | 1.89 | 11 | 289 |
| Example 14 | 0.6 | 1.2 | 0.50 | 11 | 771 |
| Example 15 | 5 | 0.7 | 7.14 | 20 | 450 |
| Example 16 | 85 | 0.45 | 188.89 | 230 | 450 |
| Example 17 | 1 | 0.45 | 2.22 | 12.9 | 289 |
| Example 18 | 0.2 | 0.8 | 0.25 | 5.5 | 514 |
| Comparative Example 3 | 338 | 0.264 | 1280.30 | 400 | 150 |
| Comparative Example 4 | 0.008 | 1 | 0.008 | 0.15 | 570 |
| Example 19 | 0.6 | 0.7 | 0.86 | 11 | 450 |
| Example 20 | 0.4 | 0.8 | 0.50 | 11 | 514 |
| Example 21 | 0.85 | 0.45 | 1.89 | 11 | 289 |
| Example 22 | 0.6 | 1.2 | 0.50 | 11 | 771 |
| Example 23 | 5 | 0.7 | 7.14 | 20 | 450 |
| Example 24 | 85 | 0.45 | 188.89 | 230 | 450 |
| Example 25 | 1 | 0.45 | 2.22 | 12.9 | 289 |
| Example 26 | 0.2 | 0.8 | 0.25 | 5.5 | 514 |
| Comparative Example 5 | 338 | 0.264 | 1280.30 | 400 | 150 |
| Comparative Example 6 | 0.008 | 1 | 0.008 | 0.15 | 570 |
| Example 27 | 63 | 0.8 | 78.75 | 800 | 120000 |
| Example 28 | 0.6 | 0.8 | 0.75 | 11 | 514 |
| Example 29 | 63 | 0.8 | 78.75 | 800 | 120000 |
| Example 30 | 320 | 0.35 | 914.29 | 1000 | 60000 |
| Example 31 | 320 | 0.3 | 1066.67 | 31000 | 60000 |
| Example 32 | 0.2 | 0.8 | 0.25 | 5.5 | 514 |

TABLE 1-continued

| | R1/R2 × 100 | Upper end of dense zone (m) | Feeding angle θ (°) | Type of powder | Powder feed rate (powder feed frequency) |
|---|---|---|---|---|---|
| Comparative Example 7 | 335 | 0.26 | 1288.46 | 1050 | 5000 |
| Comparative Example 8 | 0.0094 | 1 | 0.009 | 0.15 | 150000 |
| Example 33 | 5 | 0.7 | 7.14 | 11 | 450 |
| Example 34 | 5 | 0.7 | 7.14 | 11 | 450 |

| | R1/R2 × 100 | Upper end of dense zone (m) | Feeding angle θ (°) | Type of powder | Powder feed rate (powder feed frequency) |
|---|---|---|---|---|---|
| Example 1 | 2.4 | 7 | 45 | WO$_3$ | 0.4 kg every 5 days (6 times in 25 days) |
| Example 2 | 2.1 | 7 | 45 | | |
| Example 3 | 3.8 | 7 | 45 | | |
| Example 4 | 1.4 | 7 | 45 | | |
| Example 5 | 4.4 | 7 | 45 | | |
| Example 6 | 4.0 | 7 | 45 | | |
| Example 7 | 4.4 | 7 | 45 | | |
| Example 8 | 51.1 | 7 | 45 | | |
| Example 9 | 4.5 | 7 | 45 | | |
| Example 10 | 1.1 | 7 | 45 | | |
| Comparative Example 1 | 266.7 | 7 | 45 | | |
| Comparative Example 2 | 0.026 | 7 | 45 | | |
| Example 11 | 2.4 | 7 | 45 | AHM | 2 kg every 5 days (6 times in 25 days) |
| Example 12 | 2.1 | 7 | 45 | | |
| Example 13 | 3.8 | 7 | 45 | | |
| Example 14 | 1.4 | 7 | 45 | | |
| Example 15 | 4.4 | 7 | 45 | | |
| Example 16 | 51.1 | 7 | 45 | | |
| Example 17 | 4.5 | 7 | 45 | | |
| Example 18 | 1.1 | 7 | 45 | | |
| Comparative Example 3 | 266.7 | 7 | 45 | | |
| Comparative Example 4 | 0.026 | 7 | 45 | | |
| Example 19 | 2.4 | 7 | 45 | Catalyst | 2 kg every 5 days (6 times in 25 days) |
| Example 20 | 2.1 | 7 | 45 | | |
| Example 21 | 3.8 | 7 | 45 | | |
| Example 22 | 1.4 | 7 | 45 | | |
| Example 23 | 4.4 | 7 | 45 | | |
| Example 24 | 51.1 | 7 | 45 | | |
| Example 25 | 4.5 | 7 | 45 | | |
| Example 26 | 1.1 | 7 | 45 | | |
| Comparative Example 5 | 266.7 | 7 | 45 | | |
| Comparative Example 6 | 0.026 | 7 | 45 | | |
| Example 27 | 0.7 | 13 | 45 | WO$_3$ | 100 kg every 5 days (6 times in 25 days) |
| Example 28 | 2.1 | 13 | 45 | AHM | 400 kg every 5 days (6 times in 25 days) |
| Example 29 | 0.7 | 13 | 45 | | |
| Example 30 | 1.7 | 13 | 45 | | |
| Example 31 | 51.7 | 13 | 45 | | |
| Example 32 | 1.1 | 13 | 45 | | |
| Comparative Example 7 | 21.0 | 13 | 45 | | |
| Comparative Example 8 | 0.00010 | 13 | 45 | | |
| Example 33 | 2.4 | 7 | 88 | AHM | 2 kg every 5 days (6 times in 25 days) |
| Example 34 | 2.4 | 7 | 13 | | |

| | Utilization efficiency (%) | Yield improvment range (%) | Reactor temperature fluctuation range (° C.) |
|---|---|---|---|
| Example 1 | 48 | 0.9 | 0 |
| Example 2 | 46 | 0.8 | 0 |
| Example 3 | 49 | 1.1 | 0 |
| Example 4 | 43 | 0.8 | 0 |
| Example 5 | 56 | 1.8 | −0.5 |
| Example 6 | 58 | 1.9 | −0.4 |
| Example 7 | 58 | 1.9 | −0.4 |
| Example 8 | 50 | 1.3 | −9 |
| Example 9 | 50 | 1.2 | 0 |
| Example 10 | 35 | 0.5 | 0 |
| Comparative Example 1 | 7 | 0.1 | −16 |

TABLE 1-continued

| | | | |
|---|---|---|---|
| Comparative Example 2 | 7 | 0.1 | 0 |
| Example 11 | 32 | 0 | 0 |
| Example 12 | 30 | −0.08 | 0 |
| Example 13 | 35 | 0 | 0 |
| Example 14 | 28 | −0.07 | 0 |
| Example 15 | 40 | 0.1 | −0.5 |
| Example 16 | 37 | −0.08 | −9 |
| Example 17 | 36 | 0 | 0 |
| Example 18 | 15 | −0.2 | 0 |
| Comparative Example 3 | 5 | −0.4 | −16 |
| Comparative Example 4 | 4 | −0.5 | 0 |
| Example 19 | — | 0 | 0 |
| Example 20 | — | −0.1 | 0 |
| Example 21 | — | 0 | 0 |
| Example 22 | — | −0.1 | 0 |
| Example 23 | — | 0.2 | −0.5 |
| Example 24 | — | 0 | −9 |
| Example 25 | — | 0.1 | 0 |
| Example 26 | — | −0.2 | 0 |
| Comparative Example 5 | — | −0.4 | −16 |
| Comparative Example 6 | — | −0.4 | 0 |
| Example 27 | 60 | 2.0 | −0.1 |
| Example 28 | 37 | −0.07 | 0 |
| Example 29 | 38 | 0 | −0.2 |
| Example 30 | 35 | 0.07 | −5 |
| Example 31 | 27 | −0.1 | −10 |
| Example 32 | 10 | −0.3 | 0 |
| Comparative Example 7 | 5 | −0.4 | −10 |
| Comparative Example 8 | 4 | −0.5 | 0 |
| Example 33 | 26 | −0.07 | 0 |
| Example 34 | 25 | −0.08 | 0 |

INDUSTRIAL APPLICABILITY

According to the present invention, the process for producing unsaturated nitrile capable of sufficiently suppressing a decrease in the yield of unsaturated nitrile, and the process for producing unsaturated nitrile capable of sufficiently enhancing the yield of unsaturated nitrile by the addition of a tungsten compound can be provided. Thus, the present invention has industrial applicability in the field where such effects are expected.

REFERENCE SIGNS LIST

1: fluidized bed reactor, 2: powder, 3: internal space, 3a: sparse zone, 3b: dense zone, 4: starting material feed opening, 5: dispersion plate, 6: discharge port, 7: cyclone, 7a: inlet, 8: dispersion tube, 9: gas feed opening, 10: hopper, 11: feed pipe, 12: powder feed opening, 100: reactor, A: starting material gas, B: oxygen-containing gas, C: reaction product gas

The invention claimed is:

1. A process for producing an unsaturated nitrile comprising a reaction step of subjecting hydrocarbon to a vapor phase catalytic ammoxidation reaction in a fluidized bed reactor to produce a corresponding unsaturated nitrile,
wherein, in the reaction step, a powder is fed to a dense zone in the fluidized bed reactor using a carrier gas,
a ratio of a linear velocity LV1 of the carrier gas at a feed opening to feed the powder to the fluidized bed reactor to a linear velocity LV2 of a gas in the dense zone (LV1/LV2) is not less than 0.01 and not more than 1200,
the powder comprises one or more powders selected from the group consisting of a catalytic powder used for the vapor phase catalytic ammoxidation reaction, a powder containing a Mo compound to replenish the catalyst with Mo atoms, and a powder containing a W compound to add W atoms to the catalyst, and
the inner diameter of the fluidized bed reactor at the section corresponding to the dense zone is not less than 0.5 m$\varphi$ and not more than 20 m$\varphi$.

2. The process according to claim 1, wherein 100 times a ratio of a flow rate R1 of the carrier gas to be fed to the fluidized bed reactor to a flow rate R2 of a gas in the fluidized bed reactor (R1/R2) is not less than 0.0005 and not more than 50.

3. The process according to claim 1, wherein the linear velocity LV1 of the carrier gas is not less than 0.01 m/sec and not more than 330 m/sec, and
the linear velocity LV2 of the gas in the dense zone is not less than 0.3 m/sec and not more than 1.0 m/sec.

4. The process according to claim 1, wherein the carrier gas is an inert gas.

5. The process according to claim 1, wherein the feed opening is formed on a side wall in the fluidized bed reactor and a feeding angle of the carrier gas at the feed opening is not less than 15° and not more than 85° to a vertical direction.

6. The process according to claim 1, wherein the linear velocity LV2 of the gas in the dense zone is a linear velocity of a gas stream from the lower part in the vertical direction to the upper part in the vertical direction.

* * * * *